United States Patent [19]

Takahashi et al.

[11] 4,234,582
[45] Nov. 18, 1980

[54] TRIALKYL ISOCYANATES USED AS PESTICIDES

[75] Inventors: Hironobu Takahashi; Masamitus Honda; Yasushi Murakami, all of Tokyo; Yoshitaka Iwane, Yokohama, all of Japan

[73] Assignee: Chugai Seiyaku Kabushiki Kaisha, Tokyo, Japan

[21] Appl. No.: 32,091

[22] Filed: Apr. 20, 1979

[30] Foreign Application Priority Data

May 10, 1978 [JP] Japan ................................. 53/54436
Jul. 11, 1978 [JP] Japan ................................. 53/83522

[51] Int. Cl.³ ............................................. A01N 43/64
[52] U.S. Cl. ................................................... 424/249
[58] Field of Search ........................................ 424/249

[56] References Cited

U.S. PATENT DOCUMENTS

| | | | |
|---|---|---|---|
| 3,075,979 | 1/1963 | Tazuma et al. | 544/221 |
| 3,145,142 | 8/1964 | Lansbury | 424/249 |
| 3,376,301 | 4/1968 | Francis et al. | 260/248 |
| 3,624,252 | 11/1971 | Labarge | 424/249 |
| 3,625,964 | 12/1971 | Argabright et al. | 424/249 |
| 3,684,807 | 8/1972 | Argabright et al. | 544/221 |

FOREIGN PATENT DOCUMENTS 2622194  12/1976  Fed. Rep. of Germany .

Primary Examiner—Douglas W. Robinson
Attorney, Agent, or Firm—Browdy and Neimark

[57] ABSTRACT

A pesticide containing an effective ingredient of a trialkyl isocyanurate of the formula:

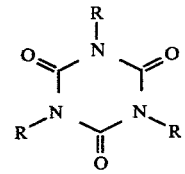

(wherein R is an alkyl group having 2 to 4 carbon atoms) which is optionally combined with a pyrethroid insecticide and a method of using the same are disclosed.

13 Claims, No Drawings

TRIALKYL ISOCYANATES USED AS PESTICIDES

BACKGROUND OF THE INVENTION

1. Field of the Invention

This invention relates to a pesticide containing an effective ingredient of a trialkyl isocyanurate of the formula (I):

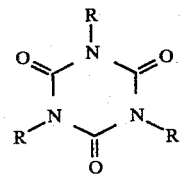

(wherein R is an alkyl group having 2 to 4 carbon atoms) which is optionally combined with a pyrethroid insecticide and a method of using the same.

2. Description of the Prior Art

Trialkyl isocyanurates to be used in this invention are known by being disclosed in prior art references, such as U.S. Pat. Nos. 3,075,979 and 3,684,807, which describe a method of producing isocyanuric acid derivatives. These prior art references contain general description of a method of preparing a trialkyl isocyanurate but they make no mention of specific examples of the ester. The references teach the use of the ester as a medicine or material from which the medicine is synthesized, insecticide, polymer or copolymer or material from which the polymer or copolymer is synthesized. However, neither U.S. Patent discloses a single example of specific uses of the trialkyl isocyanurate still less the method of using said ester as an insecticide.

The trialkyl isocyanurate to be used in this invention is also disclosed in Japanese Patent Publications Nos. 17566/60, 3985/61, 4376/61, 2556/65, 6635/65, 106/66, 9345/67, 12913/67, Japanese Patent Public Disclosure No. 6033/71, and Bulletin of the Chemical Society of Japan, 38, 10, 1586-1589, 1965. However, they only relate to a process for preparing said ester and while they teach the use of the ester as an intermediate for synthesis of an organic compound, a starting material for production of a polymer, an industrial chemical, a heating medium, a lubricant or a plasticizer, they do not state that the ester can be used as a pesticide.

SUMMARY OF THE INVENTION

As a result of various studies in search for effective use of the compound of the formula (I) above, the present inventors have found that said compound as used independently or in combination with a pyrethroid insecticide exhibits a very high ability to kill household pests such as flies, mosquitoes and cockroaches as well as agricultural vermins such as mites, tobacco cutworms, common cabbageworms, green rice leafhoppers, small brown planthoppers, aphids, scale insects and sawflies, or noxious insects that plague woods or cellulosic materials such as termites and bark beetles.

Therefore, it is one object of this invention to provide a pesticide containing an effective ingredient of a trialkyl isocyanurate of the formula (I):

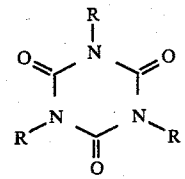

(wherein R is an alkyl group having 2 to 4 carbon atoms) which is optionally combined with a pyrethroid insecticide.

It is another object of this invention to provide a method using such novel pesticide.

DETAILED DESCRIPTION OF THE INVENTION

Table I illustrates typical examples of the compound of the formula (I) to be used in this invention. The compound identification numbers indicated in Table I are also referred to in Examples and Experiments which will be given hereinafter.

TABLE I

| ID No. | Compounds | mp. or bp. |
|---|---|---|
| 1 | triethyl isocyanurate | 106°–8° C./4mmHg |
| 2 | tri-n-propyl isocyanurate | 135°–6° C./4mmHg |
| 3 | tri-iso-propyl isocyanurate | 106° C. |
| 4 | tri-n-butyl isocyanurate | 160°–2° C./4mmHg |
| 5 | tri-iso-butyl isocyanurate | 145°–6° C./4mmHg |
| 6 | tri-sec-butyl isocyanurate | 138°–9° C./4mmHg |

The compound of the formula (I) is ingested by flies, mosquitoes and cockroaches without repellency, whereas termites and bark beetles, upon exposure to a relatively low concentration of the compound, are first repelled so that they can no longer eat into wood or cellulosic materials and thereafter they are caused to die. The compound is also systemic and therefore, by being applied into the soil or to the surfaces of plants, it is absorbed by the plant through its roots, stem, or leaves and exhibits high ability to control juice-sucking vermin at various stages of growth that parasitize the plant.

The compound also has the advantages of low toxicity to warm-blooded animals and extreme low toxicity to fish. In addition, the compound is stable to various chemical and physical conditions such as hydrolysis, heat and light, and therefore, it is subjected to substantially no limitations of the environment of application.

Examples of the suitable pyrethroid insecticide that can be used in this invention include (+)-3-allyl-2-methyl-4-oxo-2-cyclopentenyl-(+)-trans-chrysanthemate (hereunder generally referred to as "d-transallethrin"), (±)-3-allyl-2-methyl-4-oxo-2-cyclopentenyl-(±)-cis/trans-chrysanthemate (hereunder generally referred to as "allethrin"), 5-benzyl-3-furylmethyl-(±)-cis/trans-chrysanthemate (hereunder generally referred to as "resmethrin"), 5-benzyl-3-furylmethyl-(+)-cis/trans-chrysanthemate (hereunder referred to as "d-resmethrin"), N-(3,4,5,6-tetrahydrophthalimido)methyl-(±)-cis/trans-chrysanthemate (hereunder generally referred to as "phthalthrin"), and 3-phenoxybenzyl-(+)-cis/trans-chrysanthemate (hereunder generally referred to as "d-phenothrin").

The advantage of the pyrethroid insecticide illustrated above is its rapid action on the target at a small dose rate.

As described hereinabove, this invention provides a useful pesticide which comprises as an effective ingredient either only a trailkyl isocyanurate or a mixture thereof with a pyrethroid insecticide and which exhibits high residual activity plus rapid insecticidal action at a small dose rate. In addition, a trialkyl isocyanurate and pyrethroid combination is characterized not only by added activities of the individual ingredients but also by synergestic action due to the fact that the two ingredients act on different sites of a target pest through different pesticidal mechanisms.

Since both trialkyl isocyanurate and pyrethroid to be used in the pesticide of this invention are soluble in various solvents, the two ingredients can be mixed in desired proportions which vary over a wide range according to the purpose and environment of application. The trialkyl isocyanurate and pyrethroid combination of this invention work most effectively if the proportion of the pyrethroid is in the range from 2 to 40% by weight of the trialkyl isocyanurate.

In practice of this invention, the trialkyl isocyanurate which is stable and liquid at room temperature can be used per se or in the from of a composition wherein it is mixed with other effective ingredients or a vehicle. The pesticide of this invention can be applied in various forms depending upon the environment and object of application, such as a solution, wettable powder, emulsifiable concentrate, suspension, oil, powder, coat, granule, aerosol, smoke and fumigant as well as various types of mixed bait. When it is used as a mixed bait, it can advantageously assume various forms such as powder, granule, tablet, pellet, solution, suspension, emulsion, paste, and syrup by mixing with a suitable vehicle, target's favorite, or a variety of bases selected according to the environment of application. If the target is termites or bark beetles, woody substances where they live may be sprayed or injected with the pesticide of this invention or the substances may be immersed in it, depending on the case.

Solid, liquid or gaseous vehicles used singly or as a mixture may be employed to make a powder, granule, tablet or other preparation of the insecticide of this invention. Among examples of the suitable vehicle are talc, clay, bentonite, kaolin, diatom earth, calcium carbonate, potassium chlorate, niter, wood meal, nitrocellulose, starch, powder of gum arabic, alcohol, kerosine, naphtha, methyl naphthalene, xylol, benzene, acetone, air, nitrogen, carbon dioxide, Freon, vinyl chloride, propane, butane, etc.

The pesticide of this invention may also be mixed with suitable adjuvants such as a spreader, emulsifier, dispersant and a wettable spreader. It may also be combined with one or more insecticide, attractant, bactericide, preservative, herbicide, nutritive agent for plants, or fertilizer, depending upon the object of application.

It is to be understood that while the concentration of the trialkyl isocyanurate or a mixture thereof with a pyrethroid insecticide according to this invention may vary over a wide range depending upon the environment or object of application or the form in which it is used, the preferred concentration generally ranges from 0.1 to 10% by weight of the active ingredient based on the pesticidal composition. The insecticide of this invention can be applied in various manners ranging from spraying, injection or coating of woody materials with it and immersion of the same in it, up to treating the soil with it.

This invention is now described in greater detail by reference to the following experiments and examples which are given for illustrative purposes only and are by no means meant to limit the scope of this invention.

EXPERIMENT 1

Activity Test On Cockroaches

A mixed bait containing 10% of a test compound or control compound, plus control powder feed and water absorbed into an absorbent cotton were placed in a laboratory glass dish which was then placed in a synthetic resin container with lid (12 cm across and 10 cm high). Each container contained a total of 20 cockroaches of one kind (10 males and 10 females). Twenty-four hours later, the efficacy of the compounds of this invention was compared with that of controls, as shown in Table 2 below.

The control powder feed was used to demonstrate the absence of repellency of the compounds of this invention against cockroaches.

TABLE 2

| | Effect on Cockroaches (% fatality) | | | |
|---|---|---|---|---|
| | Kind of cockroaches | | | |
| Sample tested | German cockroach (Blattella germanic) | American cockroach (Periplaneta americana) | Japanese cockroach (Periplaneta japonica) | Smoky brown cockroach (Periplaneta fuliginosa) |
| Water + control powder feed | 0 | 0 | 0 | 0 |
| Mixed bait containing 10% Com. No. 1 + water + control powder feed | 100 | 100 | 100 | 100 |
| Mixed bait containing 10% Com. No. 2 + water + control powder feed | 100 | 100 | 100 | 100 |
| Mixed bait containing 10% Com. No. 5 + water + control powder feed | 85 | 90 | 90 | 90 |
| Mixed bait containing 10% Control Com. A* + water + control powder feed | 0 | 0 | 0 | 0 |
| Mixed bait containing 10% Control Com. B** + water + control powder feed | 0 | 0 | 0 | 0 |

*Control compound A: trimethyl isocyanurate
**Control compound B: tribenzyl isocyanurate
(Both controls are described in U.S. Pat. No. 3,075,979)

EXPERIMENT 2

Activity Test on Adult Oriental Housefly (*Musca Domestica vicina Macquart*)

A mixed bait containing 3% of a test compound or control compound plus control powder feed and 3% sugar water absorbed into an absorbent cotton was placed in a laboratory glass dish which was then placed in a 10×6×10 cm metal breeding cage (front, rear and bottom made of tinplate, and top as well as right and left sides made of 13 mesh metal gauze). Each cage contained a total of 20 adult houseflies (10 males and 10 females) which were 48 hours old after emergence from cocoons. Twenty-four hours later, the efficacy of the compounds of this invention was compared with that of the controls, as shown in Table 3 below.

The control powder feed was used to demonstrate the absence of repellency of the compounds of this invention against houseflies.

TABLE 3

| Effect on Housefly | |
|---|---|
| Sample Tested | % Fatality |
| 3% sugar water, control powder feed comprising sugar and milk | 0 |
| Mixed bait containing 3% Com. No. 1, control powder feed comprising sugar and milk | 100 |
| Mixed bait containing 3% Com. No. 2, control powder feed comprising sugar and milk | 100 |
| Mixed bait containing 3% Com. No. 5, control powder feed comprising sugar and milk | 80 |
| Mixed bait containing 3% Com. No. 3, control powder feed comprising sugar and milk | 85 |
| Mixed bait containing 3% Com. No. 6, control powder feed comprising sugar and milk | 80 |
| Mixed bait containing 3% Com. No. 4, control powder feed comprising sugar and milk | 90 |
| Mixed bait containing 3% Control Com. A,* control powder feed comprising sugar and milk | 5 |
| Mixed bait containing 3% Control Com. B,* control powder feed comprising sugar and milk | 0 |
| Mixed bait containing 3% Control Com. C,** control powder feed comprising sugar and milk | 0 |

*Control Compounds A and B are the same as defined in the footnote to Table 2.
**Control Compound C: tri(2-methylallyl) isocyanurate
(Either compound is disclosed in U.S. Pat. No. 3,075,979.)

EXPERIMENT 3

Activity Test on Japanese Termite (*Leucotermes speratus* Kolbe)

A circular filter paper 9 cm across was treated with 1 ml of an acetone solution containing varying concentrations of a test compound and control compound, dried in air, then impregnated with 1 ml of water, and placed in a petri dish 9 cm across. Twenty Japanese worker termites collected from a rotton wood were placed in the dish, which was covered with a glass lid and left to stand at a constant temperature of 25°±2° C. for 7 days. Table 4 below shows the time-dependent change in the number of surviving termites.

TABLE 4

| | | Effect on Japanese Termite | | | | | | | |
|---|---|---|---|---|---|---|---|---|---|
| | Concen- tration | No. of dead termites days | | | | | | | Holes* |
| Sample tested | (%) | 1 | 2 | 3 | 4 | 5 | 6 | 7 | in filter |
| Com. No. 1 | 0.2 | 20 | | | | | | | — |
| | 0.04 | 20 | | | | | | | — |
| | 0.008 | 4 | 6 | 7 | 3 | | | | — |
| Com. No. 2 | 0.2 | 20 | | | | | | | — |
| | 0.04 | 20 | | | | | | | — |
| | 0.008 | 10 | 5 | 4 | 1 | | | | — |
| Com. No. 4 | 0.2 | 20 | | | | | | | — |
| | 0.04 | 9 | 3 | 4 | 4 | | | | — |
| | 0.008 | 3 | 2 | 1 | 0 | 0 | 0 | 0 | ± |
| Control Com. | 1.0 | 0 | 0 | 0 | 0 | 2 | 1 | 1 | + |

TABLE 4-continued

| | | Effect on Japanese Termite | | | | | | | |
|---|---|---|---|---|---|---|---|---|---|
| | Concen- tration | No. of dead termites days | | | | | | | Holes* |
| Sample tested | (%) | 1 | 2 | 3 | 4 | 5 | 6 | 7 | in filter |
| A** | 0.5 | 0 | 0 | 0 | 0 | 0 | 1 | 1 | +++ |
| Control Com. | 1.0 | 0 | 0 | 0 | 1 | 2 | 1 | 1 | + |
| C** | 0.5 | 0 | 0 | 0 | 0 | 0 | 2 | 1 | ++ |
| None | — | 0 | 0 | 0 | 0 | 0 | 0 | 0 | +++ |

*—: no injury by eating;
+: small holes in filter;
++ +++: many holes in filter
**Control Compounds A and C are the same as defined in the footnotes to Tables 2 and 3.

EXPERIMENT 4

Activity Test on Formosan Termite (*Coptotermes formasanus* Shiraki)

A total of 20 test samples were prepared from 20×20×20 mm wood cubes (redpine sapwood) which were dried at 60°±2° C. for 48 hours and found to weigh $W_0$.

Ten of them were treated with Compounds Nos. 1, 2, and 4 and Control Compounds A and C and rendered weathering in the following manner, whereas the remaining ten samples were subjected to no such treatment.

Oils containing 4% of the respective compounds were prepared in accordance with the procedure described in Example 3 and the cubes were immersed in these oil preparations at 25° to 30° C. for 5 minutes, and subjected to measurement of their weights which were found to be at $W_1$. The cubes were then left to stand in a room for 20 days during which they were subjected to 10 cycles of weathering process as specified in JIS 9312, and dried at 60° C. for 48 hours, and subjected to measurement of their weights which were found to be at $W_2$.

The breeding vessel used was cylindrical glass insect breeding vessel (a diameter of 10 cm and a capacity of 500 ml) which contained 400 g of dry sand (particle size of about 0.5 to 1 mm) previously sterilized at 115° C. for 2 hours plus 80 ml of distilled water.

The test samples were placed level on the sand with their straight-grained surfaces down, and, after putting, 100 worker termites fresh from their nest into it, the breeding vessel was left to stand in a dark place at 25°±2° C. for 38 to 42 hours (RH 75%).

Thereafter, deposits were carefully removed from the surfaces of the test samples which were then left to stand at room temperature for 24 hours, dried at 60°±2° C. for 48 hours, and subjected to measurement of their weights which were found to be at $W_3$.

The following formula was used to determine the decrease in weight of the test samples due to eating by the Formosan termites:

$$\frac{W_2 - W_3}{W_2} \times 100$$

The decrease in weight and other data obtained by Experiment 4 are set forth in Table 5 below.

TABLE 5

| Test Samples | Concentra- tion (%) | Sample absorp- tion rate* (mg/cm²) | Fatality (%) | Weight loss (%) |
|---|---|---|---|---|
| Treated with | | | | |

TABLE 5-continued

| Test Samples | Concentration (%) | Sample absorption rate* (mg/cm$^2$) | Fatality (%) | Weight loss (%) |
|---|---|---|---|---|
| Com. No. 1 | 4 | 560 | 100 | 0.1 |
| Treated with Com. No. 2 | 4 | 570 | 100 | 0.1 |
| Treated with Com. No. 4 | 4 | 570 | 80 | 0.2 |
| Treated with Control Com. A** | 4 | 560 | 5 | 12 |
| Treated with Control Com. C** | 4 | 580 | 10 | 8 |
| Untreated | — | — | 0 | 15 |

* $\dfrac{W_1 - W_0}{\text{Volume of test sample}}$

**Control Compounds A and C are the same as defined in the footnotes to Tables 2 and 3.

EXPERIMENT 5

Activity Test on Green Rice Leafhopper (*Nephotettix bipuntatus cincticeps*) and Smaller Brown Planthopper (*Delphacodes striatella Fallen*)

Rice seedlings about 15 cm tall were transferred into glass conical flasks each containing 50 ml of an aqueous solution so controlled to contain a predetermined amount of a test compound or a control compound. Twenty-four hours later, each conical flask was capped with a glass cylinder (9 cm across and 20 cm high) through which 20 adult male green rice leafhoppers were placed as well as 20 adult male and female smaller brown planthoppers, and the top of cylinder was then covered with a metal gauze lid. Twenty-four hours later, the efficacy of the compounds of this invention was compared with the controls, as shown in Table 6, below.

TABLE 6

Effect on Green Rice Leafhopper and Smaller Brown Planthopper

| Sample Tested | Target Fatality (%) | |
|---|---|---|
| | Green Rice Leafhopper | Smaller Brown Planthopper |
| Water | 0 | 0 |
| Aqueous solution containing 50 ppm of Com. No. 1 | 100 | 100 |
| Aqueous solution containing 50 ppm of Com. No. 2 | 100 | 100 |
| Aqueous solution containing 75 ppm of Com. No. 3 | 100 | 100 |
| Aqueous solution containing 75 ppm of Com. No. 4 | 95 | 90 |
| Aqueous solution containing 100 ppm of Com. No. 5 | 90 | 90 |
| Aqueous solution containing 100 ppm of Com. No. 6 | 90 | 95 |
| Aqueous solution containing 200 ppm of Control Com. A* | 5 | 10 |
| Aqueous solution containing 200 ppm of Control Com. B* | 5 | 5 |
| Aqueous solution containing 200 ppm of Control Com. C* | 10 | 5 |

*Control Compounds A, B and C are the same as defined in the footnotes to Tables 2 and 3.

EXPERIMENT 6

Activity Test on Tobacco Cutworm (*Prodenia litura Fabricius*) and Cabbageworm (*Pieris rapae Linne*)

A mixed bait comprising a homogeneous mixture of an artificial feed (powdered cabbage) and a predetermined concentration of a test compound or control compound was placed in laboratory glass dishes each 9 cm across and 6 cm high. Twenty tobacco cutworms and 10 cabbageworms were then placed in each dish. Twenty-four hours later, the efficacy of the compounds of this invention was compared with that of the controls, as shown in Table 7 below.

TABLE 7

Effect on Tobacco Cutworm and Cabbageworm

| Sample Tested | Target Fatality (%) | |
|---|---|---|
| | Tobacco cutworm | Cabbageworm |
| Untreated feed | 0 | 0 |
| Mixed feed containing 2% Com. No. 1 | 100 | 100 |
| Mixed feed containing 2% Com. No. 2 | 100 | 100 |
| Mixed feed containing 2% Com. No. 4 | 100 | 100 |
| Mixed feed containing 3% Com. No. 5 | 95 | 100 |
| Mixed feed containing 3% Com. No. 3 | 100 | 100 |
| Mixed feed containing 3% Com. No. 6 | 90 | 100 |
| Mixed feed containing 5% Control Com. A* | 10 | 10 |
| Mixed feed containing 5% Control Com. B* | 5 | 10 |
| Mixed feed containing 5% Control Com. C* | 10 | 10 |

*Control compounds A, B and C are the same as defined in the footnotes to Tables 2 and 3.

EXPERIMENT 7

Activity Test on Larvae of Lyctus Powder-Post Beetle (*Lyctus brunneus Stephens*)

A solution of a given amount of each test or control compound in 0.25 μl of acetone was topically applied to the abdomen of each of 20 larvae of the beetle. The time-dependent change in fatality of the larvae is shown in Table 8 below.

TABLE 8

Effect on Lyctus Powder-Post Beetle

| Sample Tested | Dose Rate per Larva (μg) | % Fatality with Time | | |
|---|---|---|---|---|
| | | 24 hrs | 72 hrs | 120 hrs |
| Com. No. 1 | 4 | 100 | — | — |
| | 1 | 15 | 50 | 85 |
| Com. No. 2 | 4 | 100 | — | — |
| | 1 | 65 | 95 | 100 |
| Com. No. 4 | 4 | 20 | 45 | 75 |
| | 1 | 0 | 15 | 55 |
| Control Com. A* | 4 | 0 | 0 | 5 |
| Control Com. C* | 4 | 0 | 5 | 10 |
| Untreated | — | 0 | 0 | 0 |

*Control Compounds A and C are the same as defined in the footnotes to Tables 2 and 3.

EXPERIMENT 8

Activity Test on Formosan Termite

A circular filter paper 9 cm across was treated with 1 ml of an acetone solution varying containing concentrations of each of test or control compounds, dried in air, then impregnated with 1 ml of water, and placed in a petri dish 9 cm across. Twenty Formosan termite workers collected from a pine wood were placed in the dish, which was closed with a glass lid and left to stand at a constant temperature of 25°±2° C. for 96 hours. Table 9 shows the time-dependent change in the number of serviving termites.

TABLE 9

| Sample Tested | Concentration (%) | No. of dead termites | | | |
|---|---|---|---|---|---|
| | | 24 hrs | 48 hrs | 72 hrs | 96 hrs |
| Com. No. 1 | 0.4 | 15 | 5 | — | — |
| | 0.2 | 7 | 12 | 1 | — |
| | 0.1 | 0 | 12 | 3 | — |
| | 0.05 | 0 | 3 | 11 | 6 |
| Com. No. 2 | 0.4 | 20 | — | — | — |
| | 0.2 | 17 | 3 | — | — |
| | 0.1 | 4 | 16 | — | — |
| | 0.05 | 0 | 5 | 3 | 7 |
| Com. No. 4 | 0.4 | 7 | 5 | 2 | 1 |
| | 0.2 | 3 | 2 | 1 | 0 |
| | 0.1 | 2 | 1 | 0 | 0 |
| | 0.05 | 0 | 0 | 0 | 0 |
| d-Transallethrin | 0.01 | 13 | 2 | — | — |
| | 0.005 | 12 | 5 | 2 | 1 |
| | 0.0025 | 0 | 13 | 5 | 2 |
| Allethrin | 0.1 | 15 | 3 | 2 | — |
| | 0.05 | 3 | 4 | 3 | 5 |
| | 0.025 | 4 | 3 | 2 | 11 |
| Com. No. 2 plus d-transallethrin | 0.05 0.003 | 20 | — | — | — |
| Com. No. 2 plus allethrin | 0.05 0.02 | 20 | — | — | — |
| Com. No. 1 plus d-transallethrin | 0.1 0.003 | 20 | — | — | — |
| Com. No. 4 plus allethrin | 0.1 0.02 | 18 | 2 | — | — |
| Untreated | — | 0 | 0 | 0 | 0 |

EXPERIMENT 9

Activity Test on the Larvae of Lyctus Powder-Post Beetle

A solution of a given amount of each test or control compound in 0.25 μl of acetone was topically applied to the abdomen of each of 20 larvae of Lyctus powder-post beetle. The time-dependent change in fatality of the larvae is shown in Table 10 below.

TABLE 10

| Sample Tested | Dose Rate per Larva (μg) | % Fatality with Time | | |
|---|---|---|---|---|
| | | 24 hrs | 72 hrs | 120 hrs |
| Com. No. 1 | 4 | 100 | — | — |
| | 1 | 15 | 50 | 65 |
| | 0.25 | 0 | 0 | 0 |
| Com. No. 2 | 4 | 100 | — | — |
| | 1 | 65 | 95 | 100 |
| | 0.25 | 25 | 65 | 30 |
| Com. No. 4 | 4 | 20 | 45 | 55 |
| | 1 | 0 | 15 | 25 |
| | 0.25 | 0 | 0 | 0 |
| Allethrin | 4 | 90 | 100 | — |
| | 1 | 65 | 96 | 100 |
| | 0.25 | 13 | 25 | 50 |
| d-Transallethrin | 4 | 100 | — | — |
| | 1 | 72 | 93 | 100 |
| | 0.25 | 20 | 45 | 80 |
| Com. No. 2 plus allethrin | 0.25 0.25 | 75 | 100 | — |
| Com. No. 2 plus d-transallethrin | 0.25 0.25 | 85 | 100 | — |
| Com No. 1 plus d-transallethrin | 0.25 0.25 | 60 | 97 | 100 |
| Untreated | — | 0 | 0 | 0 |

EXAMPLE 1

The following ingredients were intimately blended together to form a homogeneous composition which was then ground to form a powder pesticide.

| Compound No. 4 | 1 (part by weight) |
|---|---|
| White carbon | 5 |
| Clay | 94 |

EXAMPLE 2

The following ingredients were intimately blended together to form a homogeneous composition which was used as an emulsion pesticide.

| Compound No. 1 | 50 (parts by weight) |
|---|---|
| Calcium salt of dodecyl benzene sulfonic acid | 5 |
| Polyoxyethylene alkyl allyl ether | 5 |
| Xylene | 40 |

EXAMPLE 3

The following ingredients were blended together to form a homogeneous composition which was used as an oil pesticide.

| Compound No. 2 | 4 (parts by weight) |
|---|---|
| Kawakasol (product of Kawasaki Kasei) | 96 |

EXAMPLE 4

The following ingredients were intimately blended together to form a homogeneous composition which was then ground to form a wettable powder pesticide.

| Compound No. 1 | 10 (parts by weight) |
|---|---|
| Sodium lignin sulfonate | 5 |
| Clay | 85 |

EXAMPLE 5

The following ingredients were intimately blended together to form a homogeneous composition and processed according to a conventional manner to form a granule pesticide having a particle size of 0.1 to 1 mm.

| Compound No. 2 | 5 (parts by weight) |
|---|---|
| Bentonite | 65 |
| Diatom earth | 30 |

EXAMPLE 6

The following ingredients were intimately blended together to form an oil pesticide.

| Compound No. 2 | 4 (parts by weight) |
|---|---|
| d-Transallethrin | 0.4 |
| Kawakasol (product of Kawasaki Kasei) | 95.6 |

EXAMPLE 7

The following ingredients were intimately blended together to form an emulsion pesticide.

| | |
|---|---|
| Compound No. 4 | 40 (parts by weight) |
| Allethrin | 10 |
| Calcium salt of dodecyl benzene sulfonic acid | 5 |
| Polyoxyethylene alkyl allyl ether | 5 |
| Xylene | 40 |

EXAMPLE 8

The following ingredients were intimately blended together and then ground to form a dust pesticide.

| | |
|---|---|
| Compound No. 1 | 4 (parts by weight) |
| d-Transallethrin | 0.5 |
| White carbon | 3 |
| Clay | 92.5 |

EXAMPLE 9

The following ingredients were intimately blended together to form an oil pesticide.

| | |
|---|---|
| Compound No. 2 | 2 (parts by weight) |
| d-Transallethrin | 0.1 |
| Diethyl glycol monobutyl ether | 10 |
| Zinc naphthanate | 1 |
| Aerosol Kerosine | 86.9 |

What we claim is:

1. A method for controlling household insect pests, agricultural vermin pests, and noxious insect pests that plague wood or cellulosic materials, comprising:
   placing a pesticidally effective amount, at a locus in which the pests will come into contact therewith, of a trialkyl isocyanurate of the formula $$\begin{array}{c} R \\ | \\ N \\ O \diagup \diagdown O \\ | \quad\quad | \\ N \quad\quad N \\ R \diagup \quad \diagdown \diagup \quad \diagdown R \\ \| \\ O \end{array}$$

wherein R is an alkyl group having 2–4 carbon atoms.

2. A method according to claim 1 wherein the trialkyl isocyanurate is triethyl isocyanurate.
3. A method according to claim 1 wherein the trialkyl isocyanurate is tri-n-propyl isocyanurate.
4. A method according to claim 1 wherein the trialkyl isocyanurate is tri-iso-propyl isocyanurate.
5. A method according to claim 1 wherein the trialkyl isocyanurate is tri-n-butyl isocyanurate.
6. A method according to claim 1 wherein the trialkyl isocyanurate is tri-iso-butyl isocyanurate.
7. A method according to claim 1 wherein the trialkyl isocyanurate is tri-sec-butyl isocyanurate.
8. A method in accordance with claim 1, for controlling household insect pests, wherein said trialkyl isocyanurate is placed at a locus in which the household insect pests will come into contact therewith.
9. A method in accordance with claim 8, wherein the household insect pests are flies, mosquitos or cockroaches.
10. A method in accordance with claim 1, for controlling agricultural vermin pests wherein said trialkyl isocyanurate is placed at a locus in which the agricultural vermin pests will come into contact therewith.
11. A method in accordance with claim 10, wherein the agricultural vermin pests are mites, tobacco cutworms, common cabbage worms, green rice leafhoppers, small brown planthoppers, aphids, scale insects or sawflies.
12. A method in accordance with claim 1 for controlling noxious insect pests that plague wood or cellulosic materials wherein said trialkyl isocyanurate is placed at a locus in which the noxious insect pests that plague wood or cellulosic materials will come into contact.
13. A method in accordance with claim 12, wherein the noxious insect pests that plague wood or cellulosic materials are termites or bark beetles.

* * * * *